US00PP26750P2

(12) United States Plant Patent
Hansen

(10) Patent No.: US PP26,750 P2
(45) Date of Patent: May 24, 2016

(54) ***BAPTISIA* PLANT NAMED 'INDIGO SPIRES'**

(50) Latin Name: ***Baptisia* hybrid**
Varietal Denomination: Indigo Spires

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 160 days.

(21) Appl. No.: 14/120,593

(22) Filed: Jun. 6, 2014

(51) Int. Cl.
*A01H 5/02* (2006.01)

(52) U.S. Cl.
USPC ..... Plt./263.1

(58) Field of Classification Search
USPC ..... Plt./263.1
CPC ..... A01H 5/02
See application file for complete search history.

(56) References Cited

PUBLICATIONS http://www.rarefindnursery.com/index.php/perennials/baptisia-wild-indigo/baptisia-indigo-spires-false-indigo.html; 2013; 2 pages.*

* cited by examiner

*Primary Examiner* — Kent L Bell

(57) ABSTRACT

A new and distinct plant cultivar of hardy herbaceous False Indigo named *Baptisia Baptisia* 'Indigo Spires' characterized by upright vase-shaped habit with heavily branced upright stems producing many large, dark indigo-colored flowers on well-branched stems held well above the foliage in the spring held well above the foliage in the late spring, suitable for landscaping as a specimen or en masse.

1 Drawing Sheet

Botanical classification: *Baptisia* hybrid.
Cultivar designation: 'Indigo Spires'.

BACKGROUND OF THE INVENTION

The present invention relates to a new and distinct cultivar of hybrid *Baptisia* plant, botanically known as *Baptisia* 'Indigo Spires' and will be referred to hereafter by its cultivar name, 'Indigo Spires'. The new cultivar represents a new false indigo, a hardy herbaceous perennial grown for landscape and cut flower use.

The new invention arose from a long term breeding program at a nursery in Waseca, Minn. and continued at a wholesale perennial nursery in Zeeland, Mich. with the specific intention of improving garden worthiness of perennial False Indigo plants with a wider variety of flower colors and improved garden habit.

*Baptisia* 'Indigo Spires' was a selection of a specific unreleased but unidentified proprietary seed parent of *Baptisia minor* and the male or pollen parent was an unknown *Baptisia* from an open pollinated isolation block selection consisting of proprietary complex hybrids. Also in the isolation block were advanced hybrids of *Baptisia minor* and *sphaerocarpa*.

The plant was originally selected in June of 2008 at the isolation block in Waseca, Minn., USA by the inventor. Evaluations were continued with final evaluations conducted in 2012 at a wholesale perennial nursery in Zeeland, Mich. The exact identity of the female and male parents is not known but both were from proprietary unreleased and non-patented hybrid plants containing traits of both *Baptisia minor* and *Baptisia sphaerocarpa*. Asexual propagation by cuttings was initially propagated in spring 2008 at a wholesale perennial nursery in Waseca, Minn. The results of asexual propagation are that the new plant is stable and retains its true characteristics though successive generations of asexual propagation. Propagation method for asexually reproducing plants is primarily stem cuttings. Sterile plant tissue culture can also be used for asexual propagation.

Compared to *Baptisia* 'Midnight' U.S. Plant Pat. No. 20,432, the new plant is shorter and more compact and has darker blue flowers. *Baptisia* 'Indigo Spires' also has darker blue flowers than 'Twilight' U.S. Plant Pat. No. 19,011 and much darker and more blue flowers than *Baptisia* 'Purple Smoke' (not patented).

*Baptisia* 'Indigo Spires' differs from all cultivars known to the inventor in the following combined traits:

1. Upright vase-shaped habit with thick upright stems;
2. Many large, dark indigo-colored flowers on well-branched stems held well above the foliage in the spring;
3. Dense medium to dark green foliage.

BRIEF DESCRIPTION OF THE DRAWINGS

The photographs of the new plant demonstrate the unique traits of the new plant and the overall appearance. The colors are as accurate as reasonably possible with color reproductions. Variation in ambient light spectrum, source and direction may cause the appearance of minor variation in color. The accompanying photograph is of an eight-year old plant growing in an open full-sun trial garden in Zeeland, Mich.

DETAILED BOTANICAL DESCRIPTION OF THE PLANT

Figure 1:
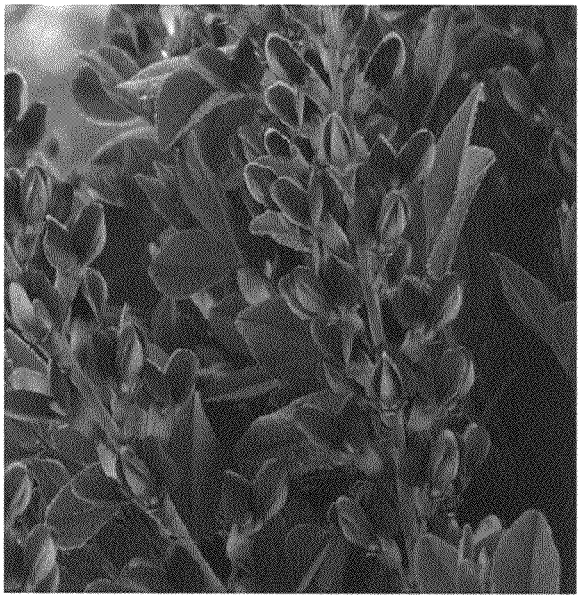
FIG. 1 shows a close-up of the flower scape.
Figure 2:
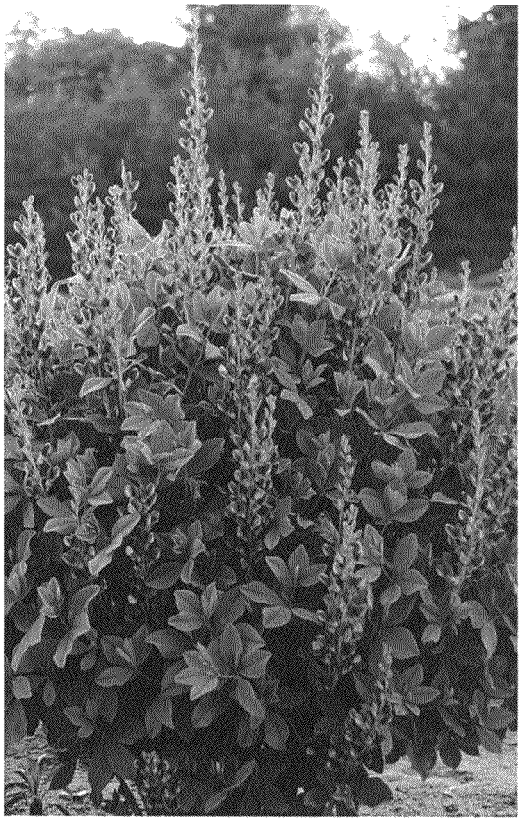
FIG. 2 shows the habit of a plant in full flower.

The following is a detailed description an eight-year old plant growing in an open full-sun trial garden at a wholesale nursery in Zeeland, Mich. Plants of the new cultivar have not been tested under all possible conditions. The phenotype may vary with changes in environment, climate, and cultural conditions without change however in the genotype. The color reference is in accordance with the 2001 edition of The Royal Horticultural Society Colour Chart except where general color dictionary terms are used.

Plant habit: Perennial, compact, well-branched, many-stemmed, vase-shaped growth habit with long inflorescences held above the foliage.

*Plant size*.—About 96 cm tall and 120 cm wide just below flowers.

Roots: Fibrous, well-branched, long, deeply rooted.

*Root color*.—Nearest RHS 161D.

Growth and propagation:

*Propagation method*.—Stem cuttings, rooting in about three weeks.

*Growth rate*.—Moderately, similar to other *Baptisia*.

Stems: Rigid and upright; glaucous; glabrous; cylindrical with longitudinal furrows; lower two to three nodes with scales and not leaves or branches; normally 36 to 48 stems per plant; main stem up to about 12 mm diameter at base and 96 cm tall to top of inflorescence, average about 80 cm tall and 11 mm diameter; normally about four alternately-arranged primary branches at 50 to 60 degree angle above horizontal, up to 65 cm long and 7.5 mm diameter at base, average for primary branches about 35 cm long and 6 mm diameter, smaller distally; and three alternately-arranged secondary branches per stem up to 35 cm long and 7.0 mm diameter at base, average about 30 cm long and 6.5 mm diameter at base; normally four alternately-arranged tertiary branches up to 12.0 cm long and 3.0 mm diameter, average about 10.0 cm long and 2.0 mm diameter.

*Stem color*.—Base without glaucous bloom between RHS 137B and RHS 137C; with glaucous bloom between RHS 122C and RHS 138C.

*Stem scales*.—At stem nodes; about 2.6 cm long and 2.2 cm wide at base; apex two short 2.0 mm sharply pointed lobes occasionally with a small tri-foliate leaf about 2.4 cm long and 1.2 cm across in the middle or without middle tri-foliate leaf; with truncate base; dehiscing to leave behind thin scar.

*Stem scale color*.—Prior to dehiscing nearest RHS 137C; after drying nearest RHS 200A.

Internodes: Up to 8.5 cm apart between middle branches, average about 4.5 cm; color of scar nearest RHS 200A.

Foliage: Alternate on stem; ternate to palmately compound with three leaflets; outer two leaflets at nearly 90 degree angle to middle leaflet; up to 7.5 cm long and 14.0 cm wide, average 5.0 cm long and 9.0 cm wide.

Leaflet: Three, oblanceolate; apex obtuse to rounded, base attenuate; margins entire; petiolate; glabrous; top surface matte, scaberulose below; size up to 7.5 cm long and 3.5 cm wide, average about 5.0 cm long and 3.2 cm wide.

*Leaflet color*.—Newly expanding nearest RHS 144A on upper and lower surfaces; mature upper and lower surface between RHS 138A and RHS 138B.

Venation: Pinnate, glabrous, thin, not conspicuous.

Vein color: Midrib on expanding foliage nearest RHS 144D above and below; midrib on mature foliage between RHS 151A and RHS N144A above and between RHS 145B and RHS 145A below; secondary veins of expanding and mature leaves same color as surrounding leaf tissue above and below.

Petioles: Glabrous; slightly glaucous; concaved facing upward, ocreate; up to about 1.0 cm long and 2.0 mm wide, decreasing distally, average 0.4 cm long and 2.0 mm wide.

*Petiole color*.—Between RHS 138B and RHS 138C on upper and lower surfaces.

Stipules: Lanceolate, acute apex with base truncate to stem; up to 1.5 cm long and 6 mm wide, average 1.0 cm long and 4.0 mm wide with largest stipules below primary branches and decreasing distally and on secondary branches.

*Stipule color*.—Nearest RHS 138A both surfaces.

Flower: Zygomorphic, papilionaceous, non-secund, held at about 40 degree angle above horizontal; beginning about 62 cm above soil; up to about 55 flowers per main raceme and about 30 per secondary branch; seasonally effective for about 3 to 4 weeks beginning in late May to early June in Zeeland, Mich. with about 28 flowers and 18 buds showing color during peak; individual flowers remain effective and on raceme for about four days; individually about 2.5 cm long, 1.6 cm tall and 1.8 cm wide at tallest and widest portions; an upper banner, a lower keel made up of two lobes folded around gynoecium and androecium; and two lateral wings or alae laterally appressed against keel.

*Flower fragrance*.—None detected.

Peduncle: Rounded with vertical furrows; glaucous; glabrous; from first flower to apex about 24 cm long; diameter at the base of first flower about 4.0 mm and about 2 mm diameter at the apex.

*Peduncle color*.—Base without glaucous bloom between RHS 137B and RHS 137C; with glaucous bloom between RHS 122C and RHS 138C.

Pedicel: Cylindrical, glabrous, slightly glaucous; about 4.0 mm long and 1.0 mm diameter.

*Pedicel color*.—Between RHS 138A and RHS 138B with tinting nearest RHS N186A.

Calyx: Flared campanulate, five-lobed with lobes dissected about 4.0 mm; top lobe apex broadly acute, other lobe apex acute; base fused in basal 3.4 mm; margins entire; slightly glaucous; about 9.0 mm long and 9.0 mm diameter; persists after petal drop.

*Calyx color*.—Between RHS 138B and RHS N144C.

Buds one to two days prior to anthesis: Oblong elliptic, flatted vertically; about 2.4 cm long and 10.0 mm tall and 6.0 mm wide.

*Bud color*.—One to two days prior to opening entire banner petal exposed darker than RHS N92A with a 2.5 diameter yellow spot nearest RHS 8B on either side of bud above the equator and just outside the calyx; exposed alae darker than RHS N92A and exposed keel along bottom and top distal region nearest RHS 2C and RHS 1A respectively.

Petals: Five; with a lower fused keel, an upper banner, and two lateral wings or alae; keel comprised of two sections that are folded around stamens and pistil.

*Banner petal*.—Conduplicate, curved upward and backward and pinched in the middle, carinate; apex retuse, base claw-like; about 2.5 cm long, 1.7 cm across at widest and 7.0 mm tall; banner dorsal side color nearest RHS N92A at perimeter with the center marginal portion lightening slightly to nearest RHS 79A, proximal 4.0 mm of base of blade nearest RHS 2C and claw nearest RHS 1B; ventral side perimeter between RHS N92A and RHS N92B, toward apex nearest RHS N92A, center ridge nearest RHS N186A, basal 2.0 mm of blade nearest RHS 3C, claw portion nearest RHS 1B.

*Keel*.—Comprised of two main lobes that are folded around stamens and pistil; fused in the distal one-third with the apex obtuse and the bases separate and claw-like; top edge about one-third of the way from base has 2.0 mm smaller lobe pointing toward base; about 24 mm long 1.5 cm across and 8.5 mm tall with claw base narrowed to 2.0 mm wide for the proximal 5.0 mm; color of outer keel sides nearest RHS 4D except distal 3.0 mm of apex nearest RHS 5D.

*Alae*.—Papilionaceous corolla appendage with rounded apex and claw-like base; with 2.0 mm lobe pointing toward base and about one-third of the way from base; about 24 mm long and 8.0 mm tall with the claw narrowed to 2.0 mm wide for the proximal 5.0 mm; color of abaxial and adaxial surfaces nearest RHS 83A; color abaxial and adaxial blade basal 3.0 mm nearest RHS 11D and RHS 11C; claw nearest RHS 1B on both surfaces.

Receptacle: Disk-shaped, about 3.3 mm diameter and 2.0 mm depth; color between RHS 144A and RHS 138A.

Gynoecium: One, with superior ovary and stipe.

*Pistil*.—About 22.0 mm long and 1.5 mm wide.

*Style*.—About 12.0 mm long and less than 1.0 mm diameter; color nearest RHS 145A.

*Stigma*.—Less than 0.5 mm diameter; color between RHS 145A and RHS 145B.

*Ovary*.—Superior suspended by stipe; about 7 mm long and about 1.5 mm in diameter; color between RHS 143A and RHS 141B.

*Stipe*.—About 3.0 mm long and 1.0 mm diameter; color nearest RHS N144C.

Androecium:

*Stamens*.—Ten, not united, about 20.0 mm long and 1.0 mm diameter.

*Filament*.—1.9 cm in length and less than 1 mm in diameter; slightly curved upward at apex; filament color nearest RHS 145C.

*Anther*.—Dorsifixed, oblong; about 1.5 mm long and 0.6 mm wide; color nearest RHS 15A.

*Pollen*.—Spherical; abundant; color nearest RHS 14B.

Fruit and seed: Have not yet been observed.

Hardiness: To USDA zones 4 to 8; heavy clay or light loamy sand soils; able to withstand drought conditions once established.

Diseases: Susceptibility or resistance to diseases beyond that typically found in other False Indigo plants has not been observed.

I claim:

1. A new and distinct cultivar of hardy herbaceous False Indigo plant named *Baptisia* 'Indigo Spires' as herein described and illustrated.

* * * * *